United States Patent [19]
Klopotek

[11] Patent Number: 6,074,385
[45] Date of Patent: Jun. 13, 2000

[54] HAIR FOLLICLE DEVITALIZATION BY INDUCED HEATING OF MAGNETICALLY SUSCEPTIBLE PARTICLES

[75] Inventor: Peter J. Klopotek, Framingham, Mass.

[73] Assignee: Kiefer Corp., Wellesley, Mass.

[21] Appl. No.: 09/017,968

[22] Filed: Feb. 3, 1998

[51] Int. Cl.[7] .................................................. A61B 18/04
[52] U.S. Cl. ................................... 606/27; 606/9; 600/9; 128/898
[58] Field of Search .................................. 606/27, 9, 28, 606/29, 30, 31, 36, 133; 60/9; 128/898

[56] References Cited

U.S. PATENT DOCUMENTS

| | | |
|---|---|---|
| 3,538,919 | 11/1970 | Mayer . |
| 3,834,391 | 9/1974 | Block . |
| 3,994,300 | 11/1976 | Siddons . |
| 4,174,714 | 11/1979 | Mehl . |
| 4,388,924 | 6/1983 | Weissman et al. . |
| 5,026,369 | 6/1991 | Cole ........................................... 606/36 |
| 5,059,192 | 10/1991 | Zaias ........................................... 606/9 |
| 5,197,940 | 3/1993 | Sievert et al. ............................... 600/9 |
| 5,226,907 | 7/1993 | Tankovich ................................ 606/133 |
| 5,411,730 | 5/1995 | Kirpotin et al. ........................... 424/322 |
| 5,425,728 | 6/1995 | Tankovich ................................... 606/9 |
| 5,468,210 | 11/1995 | Matsui et al. .............................. 600/10 |
| 5,470,332 | 11/1995 | Mehl, Sr. et al. ......................... 606/36 |
| 5,522,814 | 6/1996 | Bernaz ....................................... 606/36 |
| 5,534,003 | 7/1996 | Cole .......................................... 606/36 |
| 5,569,237 | 10/1996 | Beckenstein ................................ 606/1 |
| 5,752,949 | 5/1998 | Tankovich et al. .......................... 606/9 |
| 5,817,089 | 10/1998 | Tankovich et al. .......................... 606/9 |

FOREIGN PATENT DOCUMENTS

| | | |
|---|---|---|
| 0400940 | 12/1990 | European Pat. Off. . |
| 0756879 | 2/1997 | European Pat. Off. . |
| 2634129 | 1/1990 | France . |
| 8703798 | 7/1987 | WIPO . |

OTHER PUBLICATIONS

Kobayashi, T. et al., "Magnetic Induction Hyperthermia for Brain Tumor Using Ferromagnetic Implant with Low Curie Temperature," *Journal of Neuro–oncology*, vol. 4, 175–81 (1986).

Lilly, M. et al., "Hyperthermia Induction with Thermally Self–Regulated Ferromagnetic Implants," *Radiology*, vol. 154, 243–4 (1985).

Meijer, J.G. et al., "The Development of PdNi Thermoseeds for Interstitial Hyperthermia," *Med. Phys.*, vol. 22, No. 1, 101–4 (1995).

Montagna, W. et al., "Atlas of Normal Human Skin," Springer–Verlag (eds) 345–9 (1992).

Oleson, J., "Hyperthermia by Magnetic Induction: I. Physical Characteristics of the Technique," *Int. J. Radiation Oncology Biol. Phys.*, vol. 8, 1747–56 (1982).

Sherwood, K.A. et al., "Effect of Wavelength on Cutaneous Pigment Using Pulsed Irradiation," *J. Invest. Dermatol.*, vol. 92, 717–20 (1989).

Stauffer, P. et al., "Magnetic Induction Heating of Ferromagnetic Implants for Inducing Localized Hyperthermia in Deep–Seated Tumors," *IEEE Transactions on Biomedical Engineering*, vol. BME–31, No. 2, 235–51 (1984).

Takahashi, M. et al., "Some Considerations on Calorific Power of Soft Heating Device," *IEEE Translation Journal on Magnetics in Japan*, vol. 8, No. 2, 125–9 (1993).

(List continued on next page.)

*Primary Examiner*—Linda C. M. Dvorak
*Assistant Examiner*—R. Kearney
*Attorney, Agent, or Firm*—Thomas J. Engellenner; Nutter, McClennen & Fish, LLP

[57] ABSTRACT

Apparatus, methods, materials and systems for devitalizing hair follicles are disclosed in which magnetically susceptible particles are applied to a skin segment in a manner whereby the particles are deposited within the hair follicles and then subjected to a varying magnetic field to induce localized heating in the proximity of the particle, thereby devitalizing at least one component of the hair follicle to inhibit further hair growth.

21 Claims, 6 Drawing Sheets

OTHER PUBLICATIONS

Wilborn, W. et al., "Scanning Electron Microscopy of Normal and Abnormal Human Skin," from the Electron Microscopy Center, University of South Alabama College of Medicine, pp. 60,64 (1985).

Yanada, T. et al., "Considerations on Soft Heating Elements Utilizing Temperature Sensitive Amorphous Metal Flakes and Their Application to Local Hyperthermia," *IEEE Translation Journal on Magnetics in Japan*, vol. 7, No. 6, 494–9 (1992).

Ando, H. et al., "Characteristics of Temperature Sensitive Magnetic Powders for Soft Heating and Their Application to Hyperthermia," *IEEE Translation Journal on Magnetics in Japan*, vol. 4, No. 9, 583–9 (1989).

Chan, D. et al., "Synthesis and Evaluation of Colloidal Magnetic Iron Oxides for the Site–specific Radiofrequency–induced Hyperthermia of Cancer," *Journal of Magnetism and Magnetic Materials*, vol. 122, 374–8 (1993).

Dover, J. et al., "Pigmented Guinea Pig Skin Irradiated with Q–Switched Ruby Laser Pulses," *Arch Dermatol.*, vol. 125, 43–9 (1989).

du Vivier, A. et al., "Atlas of Clinical Dermatology," W.B. Saunders Company (eds), pp. 1.9, 1.12 (1986).

Haider, S. et al., "Power Absorption in Ferromagnetic Implants from Radio Frequency Magnetic Fields and the Problem of Optimization," *IEEE Transactions on Microwave Theory and Techniques*, vol. 39, No. 11, 1817–27 (1991).

HAIR FOLLICLE DEVITALIZATION BY INDUCED HEATING OF MAGNETICALLY SUSCEPTIBLE PARTICLES

BACKGROUND OF THE INVENTION

The technical field of this invention is the removal of hair and inhibition of hair regrowth by devitalization of certain hair structures within hair follicles.

Individual hair follicles comprise a bulb or cavity below the surface of the skin, from which a body of soft keratin is extruded. This shaft of keratin hardens as it passes through the bulb and ultimately protrudes from the skin surface as a "hair." A small cellular structure at the bottom of the cavity, the papilla, together with ancillary germinative structures, is responsible for the extrusion of the keratin which eventually forms into a hair. Permanent hair removal requires devitalization of the papilla or the structures that surround it.

The removal of body hair, a process commonly known as depilation, has been practiced with varying degrees of success for centuries by diverse methods and devices. For example, hot wax can be applied to a skin surface and allowed to harden around body hairs. Once the wax has hardened, it can be removed as a sheet, taking with it those hairs that have been entrapped by the wax. Typically, this is not a permanent process because the removal of the hair shaft does not prevent the regrowth of new hair from the shaft.

Various chemical depilatories have been used to remove hair. Typically these chemical agents are caustic, e.g., sodium hydroxide and the like, which makes the treatment process painful. Moreover, chemical depilatories are often not very effective.

Another approach to depilation is the use of electrical currents to destroy the delicate structures of the hair root. For example, U.S. Pat. No. 5,049,148 issued to Mehl discloses an electrical device of this nature. Similar devices, generally known as "electrolysis" devices have been used in various forms, with and without the assistance of chemical adjuvants. However, electrolysis is time consuming because the electrical current must be applied to each hair follicle individually.

An alternative approach for permanently impairing regrowth of many hair follicles at once is disclosed in U.S. Pat. No. 5,470,332 issued to Mehl et al. which involves the application of a conductive material to the skin's surface and then applying an electric current to this conductive layer.

Most recently, a number of techniques for photocoagulation of the delicate hair structures by laser irradiation have been disclosed. For example, U.S. Pat. No. 5,595,568 issued to Anderson et al., U.S. Pat. No. 4,388,924 issued to Weissman, et al., and U.S. Pat. No. 5,059,192 issued to Zaias disclose such laser irradiation techniques.

In addition, U.S. Pat. No. 5,425,728 and U.S. Pat. No. 5,226,907 issued to Tankovich disclose laser techniques in which the hair follicles on a section of skin are first contaminated with a substance (i.e. carbon particles) that has high absorption of light within a specific frequency band. The skin is then illuminated with such light, typically from a laser source, to heat the contaminating substance and kill the follicles or skin tissue feeding the hair root.

None of the processes described above are totally effective in depilating skin. There exists a need for better and more effective techniques. Accordingly, better methods and devices for hair removal would satisfy a long-felt need in the art.

SUMMARY OF THE INVENTION

Apparatus, methods, materials and systems for devitalizing hair follicles are disclosed in which magnetically susceptible particles are applied to a skin segment in a manner whereby the particles are deposited within the hair follicles and then subjected to a varying magnetic field to induce localized heating in the proximity of the particle, thereby devitalizing at least one component of the hair follicle to inhibit further hair growth.

In one aspect of the invention, devices are disclosed which generate a time varying magnetic field and apply such field to a region of a patient's skin that has been treated with magnetically susceptible particles.

In one embodiment, the apparatus can include a source of alternating electric current that is applied to one or more coils surrounding at least a portion of a partially open ring-ferrite structure; the structure having an open gap adapted to engage a region of a subject's skin into the follicles of which magnetically susceptible particles have penetrated. Each electrically conductive coil structure is also electrically coupled to a capacitor, such that the coil and capacitance define a resonant circuit, whereby, upon application of an electrical current to the coil, a magnetic field is formed in the gap which heats the magnetically susceptible particles within the hair follicle to induce depilation. The gap can range from about 1 millimeters to about 50 millimeters, more preferably from about 3 millimeters to about 15 millimeters.

Various other designs can be employed to deliver the time varying magnetic field to the target hair follicles. The ferrite structure need not be a simple ring but can take alternative geometric shapes designed to concentrate the magnetic field at the desired locus. A plurality of magnetic field guides can also be used. Alternatively, quasi-spherical emitters can designed to create a similar magnetic field concentration. In addition, ferrite structures can be replaced by other magnetic field guides or concentrators, such as magnetic metallic glasses and ferro-magnetic alloys. In some applications, a simple electromagnetic field generator alone can serve as a source and guide or concentrator to deliver a varying magnetic field to the desired area.

In an embodiment described in detail below, the field is generated by a resonant circuit to which a voltage is applied and a driver comprising one or more power transistors is employed to provide electronic impulses in synchrony with the frequency of the resonant circuit, thereby offsetting the energy dissipated by operation. The magnetic field guide (e.g., an open ferrite ring structure) can be readily incorporated into a handpiece which permits the clinician to manually apply the magnetic field to the treatment region. The open ring of ferrite is configured such that the gap is disposed at the tip of the handpiece in order to applied the concentrated magnetic field to the target tissue region. The handpiece can further include a coolant to extract the energy which is dissipated as heat with the field guide. The power source, driver electronics, a control microprocessor, manual controls, coolant circulator and various other auxiliary systems can be housed in a remote structure to which the handpiece is connected by one or more cables providing electrical energy and/or coolant and any auxiliary functions to the handpiece.

In another aspect of the invention, methods are disclosed to induce hair depilation by magnetic-field heating of magnetically susceptible particles deposited within hair follicles. In one method, the hair shafts in a treatment region optionally can be first extracted by wax treatment and/or tweezers.

(An anesthetic agent, such as Novocain can be applied before or after this step.) Optionally or alternatively, the skin can be cleaned to open the patient's pores. A slurry of magnetically-susceptible particles is then applied to the treatment region in a manner that facilitates deposition of such particles in to the empty spaces of the hair follicles. Deposition into the follicles can be accomplished simply by manual rubbing, or with the aid of mechanical or pressurizing instruments. (For example, a vibrating applicator can be used or a pressurized fluid (liquid or gaseous) carrying such particles can be applied to a sealed region.)

Following application of the particles and deposition of such particles into the hair follicles, the skin surface can be cleaned of any excess particles or applicator fluid. The treated region is then ready for application of the alternating magnetic field. The time-varying field induces localized heating of the particles, a portion of which will be located near enough to the papilla or other delicate structures to devitalize the hair follicle. It may also be desirable to heat the patient's skin (or monitor the skin temperature) to reduce the amount of energy that the particles need to deliver in order to kill the cells of the follicle.

The particles can then be removed (or left to be naturally cleared or metabolized by the patient's body). The use of iron oxide particles is particularly advantageous because such materials have very low toxicity and can be absorbed by the body and used as nutrients. When removal is desired, mechanical suction, aided by vibration or intermittent flushing (e.g., with water, saline or other solvents), can be employed. Alternatively, magnetic forces can be applied to extract the magnetic particles.

Such methods can further include the step of protecting any sensitive metallic implants or prostheses before the application of the magnetic field. For example, dental fillings or metal orthodontic braces may interfere with the removal of facial hair. Such structures can be protected by one or more mouth guard-type insulators which are fitted to surround any metallic dental work. The mouth guard is preferably flexible and comprises a material that possesses high magnetic shielding properties. For example, the mouth guard can be made from a plastic coated steel (or other metallic conductor).

In yet another aspect of the invention, compositions are disclosed for effecting magnetic field heating of hair structures to induce depilation. The compositions include magnetically susceptible particles having an average size sufficiently small to allow penetration of at least a portion of said particles into the follicles on the target skin segment and further having sufficient magnetic properties to induce localized heating in the presence of variable magnetic field following penetration into the hair follicle to devitalizes at least one component of the hair follicle and thereby inhibit further hair growth from within the follicle.

The compositions can include a slurry of particles having an average particle size ranging from about 5 Angstroms to about 100 micrometers in diameter, or more preferably ranging from about 50 Angstroms to about 10 micrometers in diameter. The compositions can further include particles of a lubricant material, such as surfactants, or the particles can be coated with a lubricating material, such as a surfactant, or silicone, hyaluronic compositions, dextran or combinations thereof. Such compositions can be delivered to the skin as either dry slurries or as part of fluid delivery compositions.

Fluid delivery compositions according to invention can further include a fluid carrier that enhances penetration of the particles into the hair follicles. The fluid carriers can be lotions (e.g., aqueous or non-aqueous liquids or liquid solutions, as well as emulsions, suspensions) or gaseous mixtures. Liquid lotions can include surfactants, pore opening agents or transdermal penetrating enhancing agents. Gaseous carriers can include air or other gas mixtures, typically applied to the skin under pressure to drive the magnetically susceptible particles into the skin pores and, in particular, into the lower regions of the hair follicles. Gels or semi-solid materials, such as polyvinyl alcohols, which soften or liquefy under application pressure can also serve as a delivery medium for the particles.

In yet another aspect of the invention, systems or kits are disclosed for depilating hair, including compositions for effecting magnetic field heating of hair structures to induce hair depilation and one or more of the following components: topical anesthetics, wax compositions for hair extraction, apparatus for applying a variable magnetic field to a skin region, particle/lotion applicators, penetration enhancing devices, particle removal devices and protective shield structures.

The magnetic field generating apparatus can include a source of alternating electric current, a partially-open ring-ferrite structure; the structure having an open gap adapted to engage a region of a subject's skin and permitted an electrically conductive coil structure surrounding at least an portion of the ferrite structure and electrically coupled to the source of alternating current through a capacitance, such that the coil and capacitance define a resonant circuit, whereby, upon application of the compositions containing magnetically susceptible particles to hair follicles within the skin region and the application of an electrical current to the coil, a magnetic field is formed in the gap which heats the magnetically susceptible particles to induce depilation.

The terms "depilation" and "devitalization" as used herein are intended to encompass the devitalization of hair follicles, the destruction of hair papilla (and/or associated structures), inhibition of future hair growth, or interference with any portion of the normal hair cycle. The process of depilation as taught in the present invention describes a variety of hair removal processes included, inter alia, the destruction (or substantial deactivation) of hair papilla and/or the epithelium columns that connect a growing or mature hair to the papilla; closure or modification of the hair follicle to preclude hair foliation; as well as simply the removal of the hair from the follicle. Such depilation or devitalization processes can be directed to single hair follicles or, preferably to larger areas of skin to treat a region including more than one follicle, it being understood that depilation or devitalization over any region of skin may only be partially successful during an initial treatment according to the invention and a plurality of treatments may be necessary to obtain a desired result of general hair removal from a region of a subject's body.

The term "magnetically susceptible particles" as used herein is intended to encompass a wide range of either magnetic or electrically conductive materials, which are of a size that permits their passage into hair follicles. The magnetic or electrically conductive materials which can be used herein include any non-toxic metal, including gold, silver and palladium, as well as magnetic metals such as iron and iron alloys, other conductive or magnetic metal alloys and metallic compounds which likewise possess electrical or magnetic properties. One such compound, magnetite, a magnetizable iron oxide having the general formula of $Fe_3O_4$, has proved to be particularly useful in experimental trials, but various other materials may prove to be more advantageous or useful for particular applications. The term "magnetically susceptible particles" encompasses not only materials that are inherently magnetically susceptible but also materials which become magnetically susceptible when deployed in the in vivo environment. The particles can be as small as individual molecules or ions. For example, spin transition polymers currently being developed for ultra dense magnetic memory devices may be useful. On exemplary compound magnetically susceptible particles can have the general formula: Fe-R-I * $nH_2O$, where R is atriazol, I is a cation or anion and $nH_2O$ is noncoordinated water.

Typically, the average size (i.e., the diameter or length of the longest dimension for non spherical shapes) of the magnetically susceptible particles can vary from about 5 Angstroms to about 100 micrometers, and more preferably from about 50 Angstroms to about 10 micrometers. The magnetically susceptible particles can be applied to the skin as a powder, in a liquid or as part of a lotion. Within a particular powder, liquid or lotion the size of the particles can range by more than one, or even two, orders of magnitude; the only critical factor being that a sufficient number of the magnetically susceptible particles should be capable of entering the hair follicle cavity and lodging in positions that facilitate depilation.

The term "magnetically-susceptible particles" is also used herein to encompass coated particles as well as molecular structures that incorporate any of the above referenced elements or compounds. Coating materials can include surfactants, polysaccharides, such as dextran, as well as ficolls, silicones, chondroitin sulfates, dextrane sulfates, laurates, inulins, and xylans. Molecular structures can include ferritins, hemosiderins and similar materials which comprise a spherical protein cage in which iron is stored (e.g., in the form of iron(III)oxyhydroxide). Colorants can also form part of the particles.

A presently preferred embodiment comprises a coated magnetite powder. Such powders are available from a variety of sources. For example, magnetite powders are available from Ferrofluidics Corporation (Nashua, N.H.) and/or Toda America Incorporated (Schaumburg, Ill.). As noted above, the average size of individual magnetite particles can vary in size from about 10 angstroms to about 100 micrometers in diameter. The initial susceptibility of such particles ($4\pi M/H$) can range from about 0.1 to 0.9 EMU/gauss/gFe.

It should be appreciated that the formula $Fe_3O_4$ for magnetite is an empirical formula. Magnetite is more precisely described as a crystalline metal oxide having two components: FeO and $Fe_2O_3$. Two different valence iron ions occupy specific sites in the crystal structure. The A metal is Fe+2 and the B metal is Fe+3. The arrangement causes a transfer of electrons between the different irons in a structured path or vector. This electric vector generates the strong magnetic field associated with native magnetite ores. Although magnetite is a presently preferred material for the magnetically susceptible particles of the present invention, various other materials may also be useful, including, for example, iron hydroxides, cobalt-$Fe_3O_4$, barium ferrites, and metallic iron particles.

Superparamagnetic particles (e.g. with initial susceptibilities greater than 0.5 EMU/gauss/gFe and/or negligible coercivity) can also be used. One such composition, a gamma ferric oxide, is disclosed in U.S. Pat. No. 5,411,730 issued to Kirpotin et al on May 2, 1995 and incorporated herein by reference. This patent also describes various techniques for coating particles to form ferroliposomes and the like which can be generally applicable to the present invention.

Colloidal suspensions of magnetite, coated with one or more surfactants, are also available from Ferrofluidics Corporation. More generally, suspensions of magnetically-susceptible particles can be formed with water, water/alcohol mixtures or multiphasic liquids as the carrier. Suspensions useful in the present invention can vary in viscosity from about 1 centipoise to about 100,000 centipoise with magnetite concentration varying from about 0.5 volume percent to about 20 volume percent (yielding magnetic flux densities from about 20 gauss to about 1,000 gauss). One exemplary composition can be formed by coating magnetite particles with a cationic surfactant and suspending such coated particles in a water/ethanol mixture. In other applications, anion, amphoteric or non-ionic surfactants may be preferred.

Lotions useful in the applying the magnetically susceptible particles to the skin can include aqueous and/or organic (e.g., oily or alcohol) fluids, as well as emulsions having both aqueous and non-aqueous phases. The lotions are preferably chosen because of their ability to promote penetration of the magnetically susceptible particles into the cavities of the hair follicles. In some applications a proper balance of hydrophobic and hydrophilic components may be optimal in assisting penetration. In other applications the addition of an electrically charged component or the presence of chemical additives with chemical moieties that present a surface electrical charge can be useful. In yet other embodiments, it can be useful to employ lubricants such as silicones or hyaluronic compositions, either as coatings for the particles or as additional components of the lotion to enhance lubricity. Alternatively, chemical agents that induce expansion of the hair follicle openings can be useful.

Thus, the term "lotion" as used herein is intended to encompass solutions, such as aqueous and organic solvent solution and well as suspensions, emulsions and the like which serve as carriers for a magnetically susceptible particle or plurality of such particles. In one embodiment the lotion can be an aqueous solution including a surfactant. In another embodiment, the lotion can be a mixture of water and alcohol or a mixture of water and aliphatic liquid. Alternatively, the lotion can be an oil alone or in conjunction with an emulsifying agent that ensures a uniform distribution of magnetically susceptible particles. The lotions can further include colorants, transdermal enhancing agents, as know in the art, and pore opening agents, likewise known in the art, to facilitate hair follicle penetration.

In the present invention, the application of the varying magnetic field to the magnetically susceptible particles induces rapid and extremely localized heating in the region of immediately surrounding the particles. Although no one theory of explanation may be entirely correct in analyzing this heating effect, it appears that the orientation and reversal of domain polarities in magnetic materials as well as the creation of eddy currents in conductive materials both play a role in the superheating of the particles. When a particle is disposed within the hair follicle, the heat generated by the particle is sufficient to destroy or devitalized the follicle's internal structures necessary for hair growth.

"Alternating current" as used herein is intended to encompass not only sinusoidal waveforms, but also various other waveforms, such as pulsed, square wave, ramped, saw tooth, chirped waveforms and the like. The particular shape of the waveform is largely irrelevant so long as it can induce a variable magnetic field in the target skin region where magnetically susceptible particles are heated to achieve the desired depilatory effect on hair follicles. Similarly, the term "variable field" is intended to encompassed not only reversals of polarization but also pulsed fields and any other magnetic field that changes over time in a manner that permits the transfer of energy from the power supply to the magnetically-susceptible particles. The frequency of alternation or variation can vary from about 1 kilohertz to about 10 gigahertz, preferably from about 10 kilohertz to about 100 megahertz, and, in some applications, it may be preferable to vary the frequency from about 20 kilohertz to about 20 megahertz or from about 50 kilohertz to about 3 megahertz.

Ferrite cores useful in channeling magnetic field lines can be obtained from various sources including Magnetics, Inc. (Butler, Pa.); TDK Corporation (Tokyo, Japan) or U.S. Philips Corporation (New York, N.Y.). Ferrites useful in the present invention encompass ferromagnetic compounds and iron-containing compositions generally (including ferromagnetic alloys and magnetic metal glassses) which exhibit high magnetic permeability and also high electrical resistivity. One example of such materials is the 3F3 Ferrite manufactured by U.S. Philips Corporation. The ferrite preferably is capable of generating a magnetic field of at least 0.02 Tesla and, more preferably, a field greater than about 0.3 Tesla. In some applications a ferrite core may not be necessary and instead can be replaced by an air coil (e.g. a torroidal coil) or other arrangements that can serve as magnetic field guides.

The term "Curie temperature" or "$T_c$" as used herein is used as a measurement of temperature (or temperature range) where magnetically susceptible materials undergo a rapid change in their properties. For many of the magnetically susceptible materials useful in the present invention it represents a plateau point beyond which additional exposure to the variable magnetic field will not induce significant additional heating effects. In applications where a lotion containing a substantial quantity of magnetically susceptible particles is applied and penetrates into the skin, it is desirable that the particles themselves exhibit a high enough Curie temperature to devitalize the follicle by local heating effects but not induce significant thermal damage to surrounding dermal structures. In some embodiments of the present invention, the Curie temperature of the magnetically susceptible particles useful in the present invention is preferably greater than about 45° C., more preferably greater than about 60° C., and most preferably greater than about 75° C., but less than 600° C.

However, in other applications of the invention where the heating is very localized, the Curie temperature of the particles can be much greater, so long as the total application of depilating energy does not have significant adverse effects on surrounding tissue regions. Magnetite is an example of a very high Curie temperature material that is, nonetheless, particularly useful in certain applications of the invention.

The invention will next be described in connection with certain illustrated embodiments; However, it should be clear that various changes and modifications can be made by those skilled in the art without departing from the spirit and scope of the invention.

BRIEF DESCRIPTION OF THE DRAWINGS

The invention may be more fully understood from the following description when read together with the accompanying drawings in which:

FIGS. 4A–4E illustrate a method of hair follicle devitalization according to the invention.

DETAILED DESCRIPTION

Figure 1:
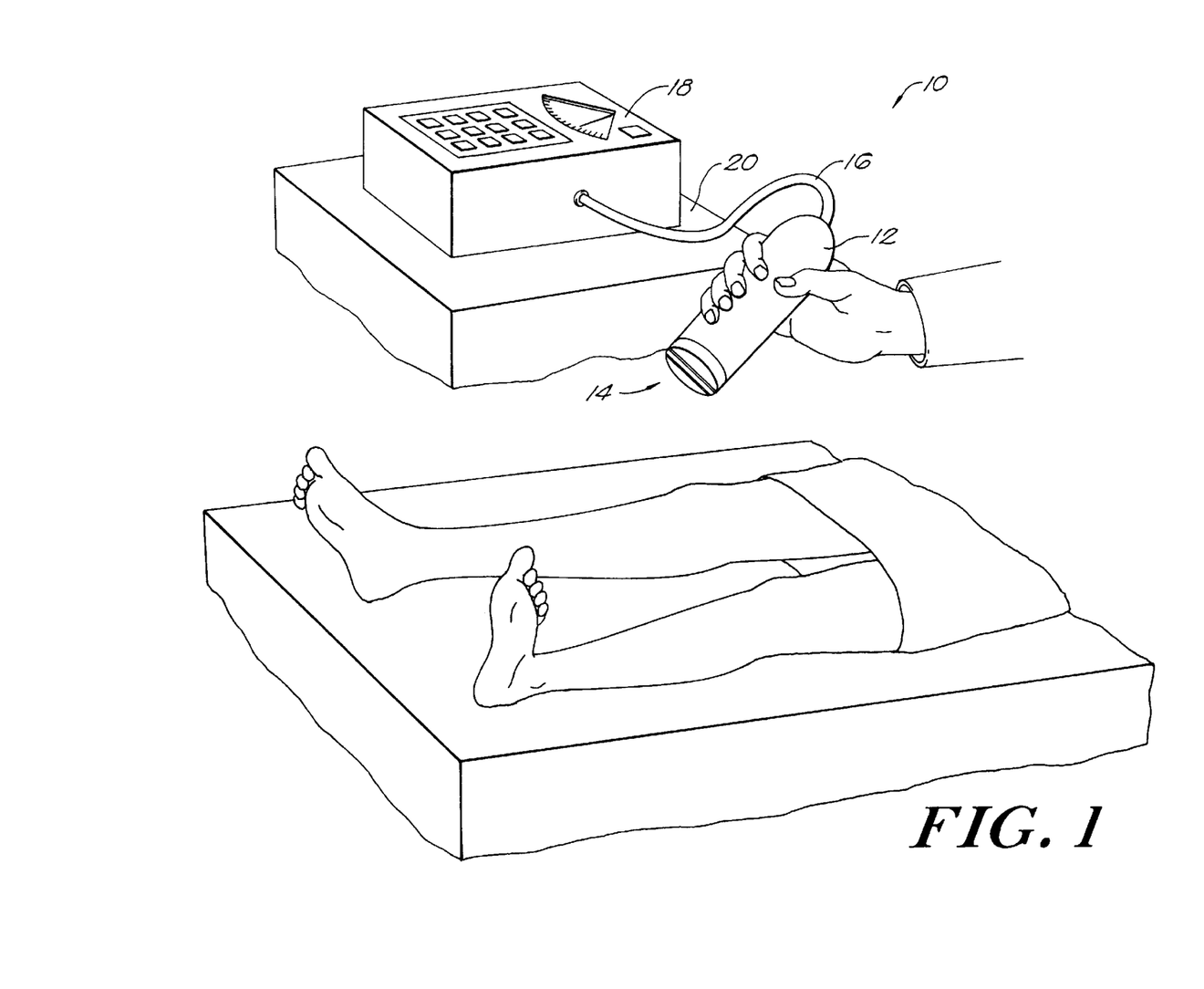
FIG. 1 is a schematic illustration of a system according to the invention for magnetic devitalization of hair follicles in a skin segment.

In FIG. 1, a system 10 for magnetic follicle devitalization is shown comprising a handpiece 12 which houses a magnetic field generating open-ring ferrite structure. The opening is oriented such that the opening in the ring forms a gap 14 at the distal end of handpiece 12. The handpiece is connected via conduit 16 to a controller 18 and an auxiliary housing 20 (which can include driver electronics, a control microprocessor, manual controls, a coolant circulator and various other auxiliary systems).

Figure 2:
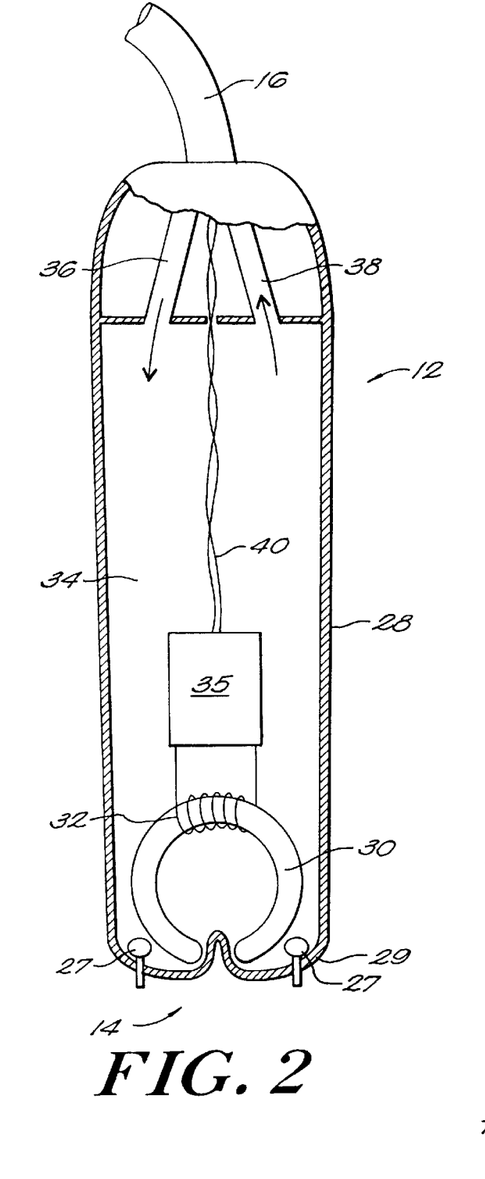
FIG. 2 is a more detailed cross-sectional schematic illustration of an apparatus for delivering a varying magnetic field according to the invention.

In FIG. 2, the handpiece 12 of FIG. 1 is shown in more detail including the ferrite ring structure 30, an inductive coil 32 which is wrapped around the ferrite core and a capacitor and/or other electronics 35. Power to generate a magnetic field within the ferrite 30 can be supplied from the housing 20 (shown in FIG. 1) via electrical cables 40. The handpiece can also incorporate an internal cooling chamber 34 which is supplied with coolant via a coolant source conduit 36. The coolant circulates within the chamber 34 to extract heat which otherwise would build up in the ferrite ring 30. Heated coolant can be withdrawn from the handpiece via a coolant exit conduit 38 for recycling within the housing or disposal. The electrical cables as well as the coolant supply and extraction conduits can all be encased within a single tubing 16 (or, alternatively, separate cables can be employed for electrical power and coolant delivery). The shell 28 or rim 29 of the handpiece 12 can also be used to heat the patient's skin. The rim 29 can also include a marker mechanism (e.g., an ink application) 27 which serves to delineate areas which have been treated.

The electronic circuitry 35 within the instrument (in cooperation, if necessary, with an auxiliary processor within housing 20) can also include an electronic sensor for metallic implants such as dental work (e.g., metallic fillings and/or orthodontic braces) that may need to be protected if the treatment region is in close proximity to such an implant.

Figure 3:
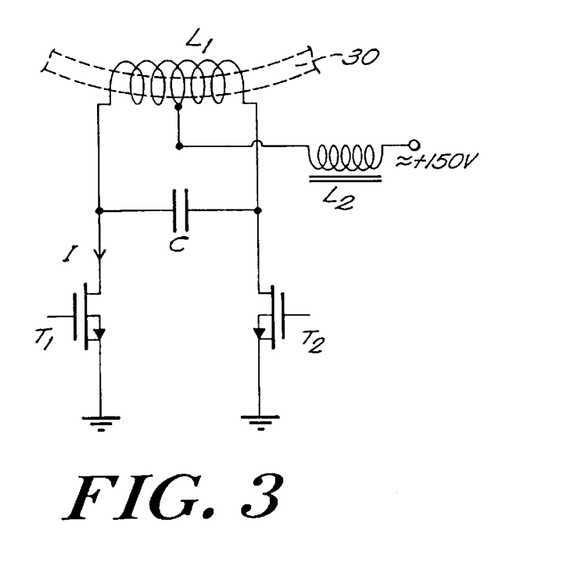
FIG. 3 is a schematic diagram of a driver circuit for the apparatus of FIG. 2.

In FIG. 3, an electrical schematic diagram of a driver circuit for the magnetic field-generating ferrite ring 30 is shown comprising the inductive coil labeled "$L_1$" in the drawing. As shown, it consists of 6 turns of wire about the ferrite torroid 30 (shown in phantom). The inductor $L_1$ is connected to capacitor C, as shown, and supplied with a current via a center tap. Power transistors $T_1$ and $T_2$ serve to inject additional energy into the circuit as energy is lost (as heat) in the ferrite core 30 and/or other components of the circuit. In one illustrative embodiment, about 2 amperes is supplied via choke $L_2$ to the center tap. The choke $L_2$ can have an inductance of 350 microhenries and the 6 turn inductor $L_1$ can have an inductance of about 3.5 microhenries. The capacitor C can have a capacitance of about 0.08 microfarads. Power transistors $T_1$ and $T_2$ are N-channel MOSFET transistors (Model No. IRFP460LP) available from the International Rectifier Corporation.

Together the inductance $L_1$ and the capacitors C form a resonant circuit with approximately 70 amperes of current flowing back and forth. Preferably, the resonant circuit of the coil $L_1$ and capacitance C has a Q factor over 10. The opening and closing of transistors $T_1$ and $T_2$ are timed to synchronize with the resonant frequency of the LC circuit. The ferrite core can be a open-toriroidal structure (with a gap of about 7 mm) made, for example, from 3F3 ferrite material available from the U.S. Phillips Corporation. This current-fed resonant push-pull circuit serves to generate an oscillating magnetic field within the ferrite ring 30 (and across the gap) at the same frequency as the resonant LC circuit.

All matter exhibits magnetic properties when placed in an external magnetic field. Even non-magnetic metals, such as copper and aluminum, are affected by the presence of a magnetic field. Materials that are attracted to the pole of a magnet are classified as paramagnetic, while those that are repulsed are classified as diamagnetic. Materials, such as iron, that exhibit a very strong attraction towards the pole of a magnet are further classified as ferromagnetic. Whether a substance is paramagnetic or diamagnetic depends primarily on the presence or absence of free magnetic dipole moments in the material's constituent atoms.

Because paramagnetic materials have free magnetic dipole moments, the presence of a magnetic field will induce alignment of the normally randomly aligned moments (or domains) of the material. When an alternating magnetic field is applied to such materials, the dipoles will attempt to reverse their orientation. As the dipoles are cycled back and forth, heating occurs at the microscopic level until a certain temperature (dependent on the material) is reached. This temperature is typically referred to as the Curie temperature and represent a plateau for many materials at which they exhibit minimal responses to further magnetic excitation.

In one embodiment the present invention can take advantage of this property of magnetically susceptible materials by "tuning" the frequency and duration of the varying magnetic field to ensure that the magnetically susceptible particles are rapidly brought to their Curie temperature and held there only for a period of time sufficient to induce apotosis of the hair papilla and/or other hair structures.

In another embodiment of the invention, heat is generated by interaction between the magnetically susceptible particle and a fluid carrier. When such a magnetically susceptible particle is exposed to an alternating or rotating magnetic field while it is in a fluid, the particle will be induced to rotate or swing into alignment with the field. The mechanical friction between the particle and the fluid dissipates the field energy as heat in fluid surrounding the particle. The optimal frequency for heating will depend upon the particle's magnetic movement, its moment of (rotational) inertia and, to some extent, the viscosity of the surrounding fluid. At frequencies above the optimal frequency (for a particular particle and fluid composition) the moment of inertia for individual particles will inhibit heating because the particles will be unable to swing in response to such high frequencies.

Figure 4A:
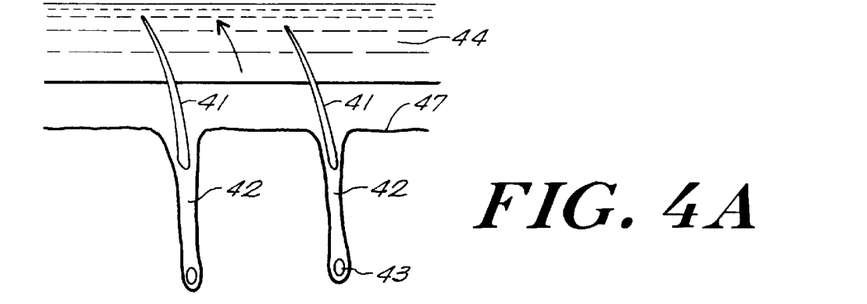
FIG. 4A shows an optional initial step of removing hairs from a skin surface.

FIGS. 4A–4E illustrate a method of hair follicle devitalization according to the invention. In FIG. 4A, hair shafts 41 are removed from the lumens or cavities 42 of hair follicles. The hair shafts 41 can be removed, for example, by the application of a hot liquid wax 44 and, after solidification, removal of the wax 44 from the patient's skin. Alternatively, tweezers or other mechanical instruments can be employed to remove hair shafts from the treatment site.

Figure 4B:
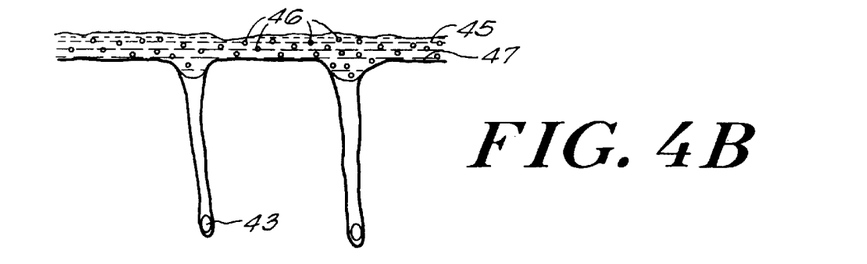
FIG. 4B illustrates the application of magnetically susceptible particles to the skin surface.
Figure 4C:
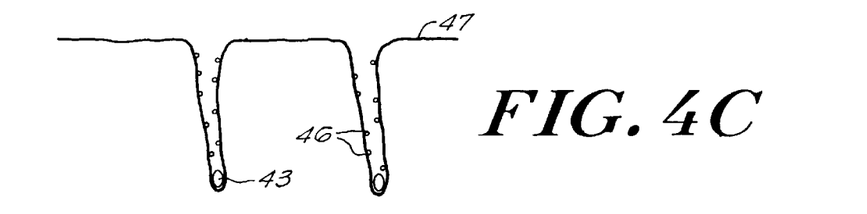
FIG. 4C illustrates the migration of magnetically susceptible particles into the hair follicles and the removal of any excess magnetically susceptible particles and/or carrier fluid from the skin surface.

In FIG. 4B, a slurry or lotion 45 containing magnetically susceptible particles 46 is applied to the surface of the skin 47. Following application, a portion of the slurry or lotion (and the magnetically susceptible particles) penetrate into the individual hair follicles as shown in FIG. 4C. Once penetration is achieved, the excess slurry or lotion can be removed from the patient's skin surface 47.

Figure 4D:
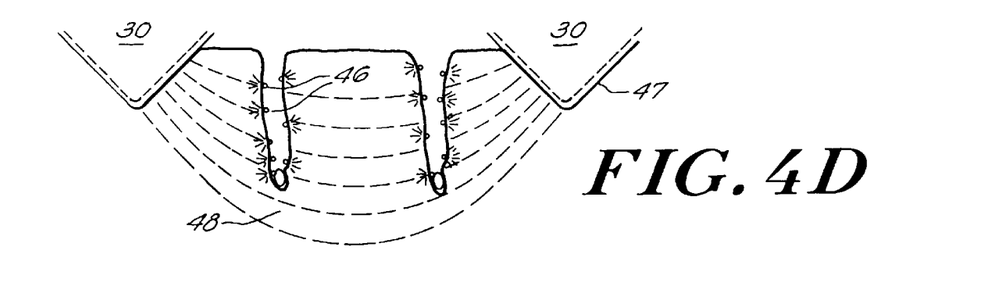
FIG. 4D shows the application of a varying magnetic field to induce heating of the particles.

In FIG. 4D, the magnetic field generating apparatus of the present invention is applied to the skin. As illustrated, a ferrite ring structure 30 (shown in phantom) is pressed against the skin causing a slight indentation and squeezing the treatment area into the gap region 48 such that the magnetically susceptible particles 46 are subjected to the magnetic field 48. (It should be appreciated that the magnetic field generator can engage the skin without direct contact. In some embodiments, engagement can be achieved by simply aiming the magnetic field generator at the target skin region. The term "engage" as used herein is intended to encompass both physical contact and non-contact relationships—in which the magnetic field is applied by an instrument at some distance from the treatment area.) The alternating current of the applicator causes a varying magnetic field in the gap region 48 and induces localized heating of particles 46. One or more particles disposed within the cavity of the follicle is sufficient to devitalize it by heating effects, as shown in FIG. 4D.

Figure 4E:
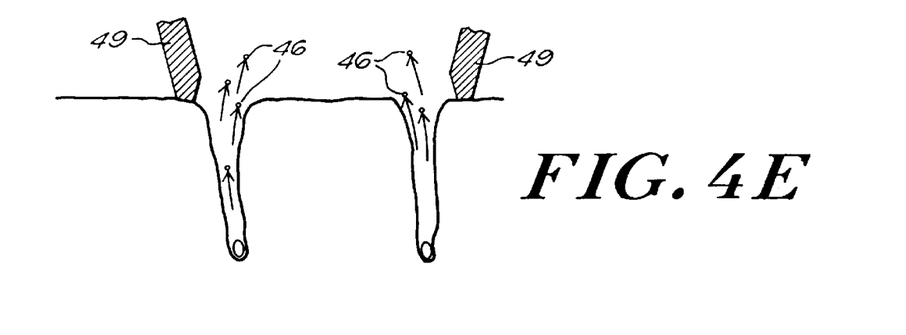
FIG. 4E illustrates the optional further step of removing the particles from the follicles following treatment.

In FIG. 4E the magnetically susceptible particles 46 can be removed with a removal apparatus 49, employing either suction or magnetic forces to dislodge and detract the magnetic particles following treatment, as shown in FIG. 4E.

Figure 5:
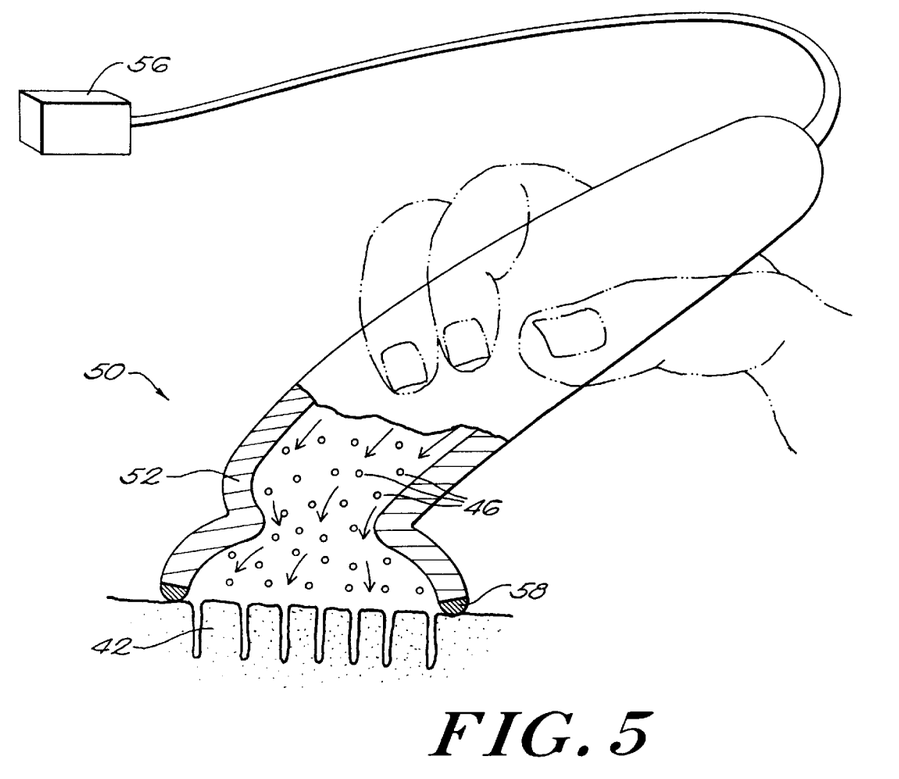
FIG. 5 illustrates an apparatus for applying magnetically susceptible particles to follicles in a skin segment.

In FIG. 5, a applicator structure 50 is shown comprising a hand-held housing 52 and a source 58 of magnetically susceptible particles 46. Particles can be driven into the skin by pressure. The air or fluid pressure supplied by instrument 50 causes at least a portion of the magnetically susceptible particles to penetrate into the cavities 42 of the hair follicles. A sealing rim 59 can also be incorporated.

Figure 6:
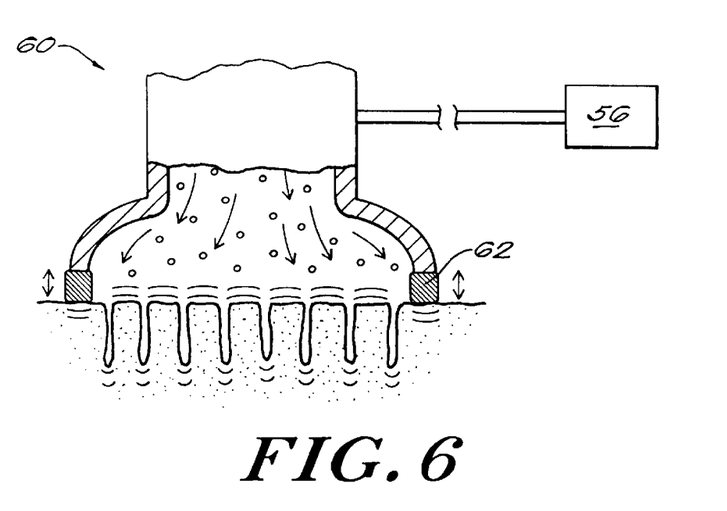
FIG. 6 illustrates an alternative apparatus for applying magnetically susceptible particles to follicles in a skin segment.

In FIG. 6, an alternative applicator 50A is shown which includes a vibrating rim 62. The instrument 50A not only can apply air or fluid pressure to induce particle penetration but the vibration of rim element 62 further enhances the penetration of the magnetically susceptible particles 46 into the cavities 42.

Figure 7:
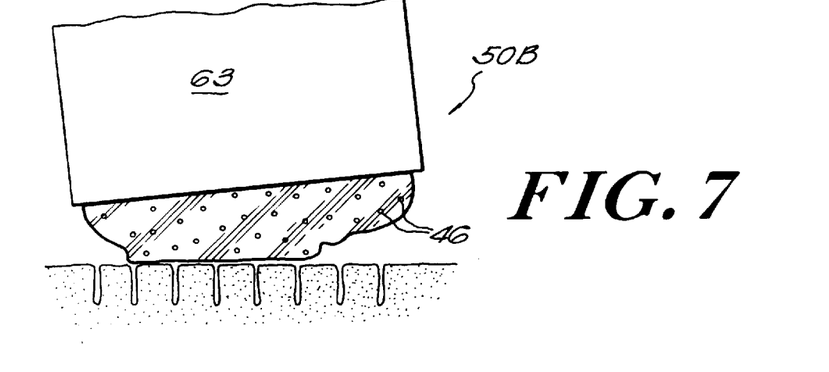
FIG. 7 illustrates another alternative apparatus for applying magnetically susceptible particles to follicles in a skin segment.

In FIG. 7 yet another applicator 50B is shown in the form of a hand held reservoir 63 for magnetic particles 46 in a polymeric matrix 65. The applicator 50B can be similar in form and composition to deodorant sticks and employ a semi-solid or gel carrier (such as a polyvinyl alcohol) which changes viscosity upon application of pressure to release the particles into the follicle cavities.

Figure 8:
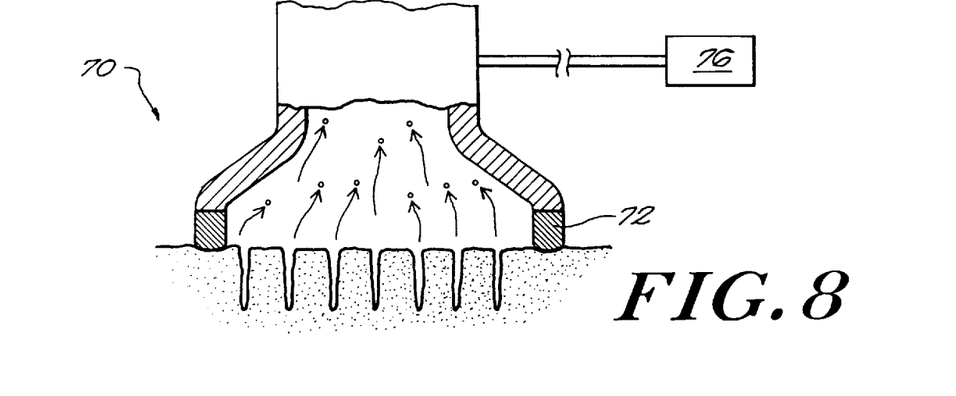
FIG. 8 illustrates an apparatus for removing magnetically susceptible particles from follicles in a skin segment.

In FIG. 8, a particle extraction device 70 is shown which employs a rim gasket (or oscillating ring element) 72 to isolate the region from which the magnetic particles will be extracted following therapy. The lumen of the instrument 70 can be connected to pump 76 supply suction or, alternatively, a combination of flushing and suction to facilitate particle removal.

Figure 9:
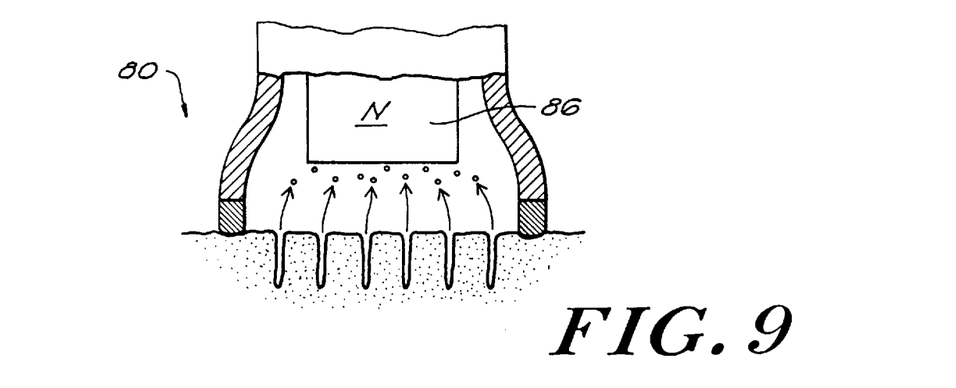
FIG. 9 illustrates an alternative apparatus for removing magnetically susceptible particles from follicles in a skin segment.

In FIG. 9, yet another embodiment of a removal apparatus 80 is shown including not only a suction function but also a magnet 86 which can be either a permanent or oscillating electromagnet which further assists in the removal of the magnetically susceptible particles by magnetic attraction. This magnetic attraction function can, of course, be combined with either suction or flushing and/or mechanical vibration of the skin to cooperate in the removal of the particles 46.

Figure 10:
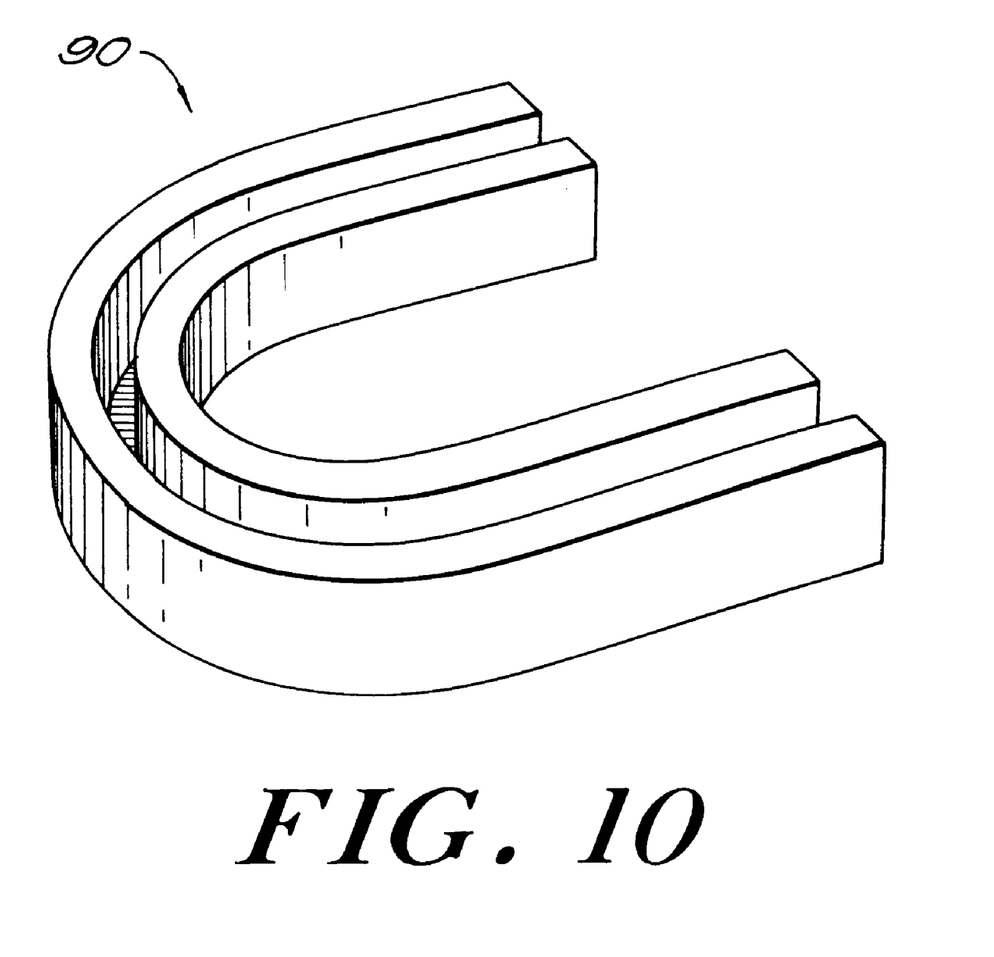
FIG. 10 illustrates a protective cover for dental work when removal of facial hair is desired.

In FIG. 10 another auxiliary component of the invention, a protective covering 90 is shown. This protective covering 90 is specifically adapted to protect a patient's dental work (e.g., metallic fillings and/or orthodontic braces) during the removal of facial hair. The instrument 90 is shaped in the form of a mouth guard and has a curved groove into which a patient's teeth can be inserted. (Although a single mouth guard for an upper set of teeth is shown in FIG. 9, it should be clear that similar devices can also be employed for protection of the patient's lower set of teeth and other forms can be used to protect other portions of the patient's body.) Preferably, the instrument 90 is made of a malleable plastic material and is filled internally with a substance (e.g., a metal or other electrically conductive material) that effectively shields the teeth from magnetic fields.

I claim:

1. A method of devitalizing a hair follicle on a skin segment, comprising,
    applying magnetically susceptible particles to the skin segment in a manner whereby at least one magnetically susceptible particle is deposited within a hair follicle;
    subjecting said deposited particle to a varying magnetic field to induce localized heating in the proximity of the particle such that said heat devitalizes the hair follicle to inhibit further hair growth.

2. The method of claim 1 wherein the method further comprises applying a slurry containing said magnetically susceptible particles to the skin segment such that penetration of the hair follicle occurs by infiltration.

3. The method of claim 1 wherein the magnetically susceptible particles are applied to the skin segment by applying a lotion containing magnetically susceptible particles onto the skin segment.

4. The method of claim 1 wherein the method further comprises initially removing the hair shafts from the follicles so that the cavities of the hair follicles are exposed.

5. The method of claim 4 wherein the step of removing the hair shafts further comprises applying a wax to the skin and then removing the wax with the hair shafts entrained therewith.

6. The method of claim 1 wherein the method further comprises applying a chemical hair defoliant agent prior in order to remove at least some the hair shafts prior to applying the magnetically susceptible particles.

7. The method of claim 1 wherein the method further comprises applying a cleaning agent prior to applying the magnetically susceptible particles.

8. The method of claim 1 wherein the method further comprises applying a degreasing agent prior to applying the magnetically susceptible particles.

9. The method of claim 1 wherein the method further comprises drying the skin segment prior to applying the magnetically susceptible particles.

10. The method of claim 1 wherein the method further comprises applying a vibrational force to the skin segment to enhance the penetration of magnetically susceptible particles into the hair follicles.

11. The method of claim 1 wherein the method further comprises applying a fluid pressure to the skin segment to enhance the penetration of magnetically susceptible particles into the hair follicles.

12. The method of claim 1 wherein the method further comprises applying a magnetic field to the skin segment to enhance the penetration of magnetically susceptible particles into the hair follicles.

13. The method of claim 1 wherein the method further comprises marking the skin segment following treatment.

14. A method of devitalizing a hair follicle on a skin segment, comprising,
    applying magnetically susceptible particles of a material having a magnetic susceptibility of at least 0.1 EMU/gauss/gFe to the skin segment in a manner whereby at least one magnetically susceptible particle is deposited within a hair follicle;
    subjecting said deposited particle to a varying magnetic field to induce localized heating in the proximity of the particle such that said heat devitalizes the hair follicle to inhibit further hair growth.

15. The method of claim 14 wherein the step of applying magnetically susceptible particles to the skin segment further comprises applying particles of a material having a magnetic susceptibility of at least 0.3 EMU/gauss/gFe to the skin.

16. A method of devitalizing a hair follicle on a skin segment, comprising,
    applying magnetically susceptible particles of a paramagnetic material to the skin segment in a manner whereby at least one magnetically susceptible particle is deposited within a hair follicle;
    subjecting said deposited particle to a varying magnetic field to induce localized heating in the proximity of the particle such that said heat devitalizes the hair follicle to inhibit further hair growth.

17. A method of devitalizing a hair follicle on a skin segment, comprising,
    applying magnetically susceptible particles of a metal-containing material to the skin segment in a manner whereby at least one magnetically susceptible particle is deposited within a hair follicle;
    subjecting said deposited particle to a varying magnetic field to induce localized heating in the proximity of the particle such that said heat devitalizes the hair follicle to inhibit further hair growth.

18. The method of claim 17 wherein the step of applying magnetically susceptible particles to the skin segment further comprises applying particles of an iron-containing material to the skin.

19. The method of claim 17 wherein the step of applying magnetically susceptible particles to the skin segment further comprises applying particles of magnetite to the skin.

20. A method of devitalizing a hair follicle on a skin segment, comprising,
    applying magnetically susceptible particles of a material having a Curie temperature of at least 45 degrees to the skin segment in a manner whereby at least one magnetically susceptible particle is deposited within a hair follicle;
    subjecting said deposited particle to a varying magnetic field to induce localized heating in the proximity of the particle such that said heat devitalizes the hair follicle to inhibit further hair growth.

21. A method of devitalizing a hair follicle on a skin segment, comprising, applying magnetically susceptible particles of a material coated with a surfactant to the skin segment in a manner whereby at least one magnetically susceptible particle is deposited within a hair follicle;

subjecting said deposited particle to a varying magnetic field to induce localized heating in the proximity of the particle such that said heat devitalizes the hair follicle to inhibit further hair growth.

* * * * *